United States Patent [19] … [11] Patent Number: 5,177,091
Feige et al. … [45] Date of Patent: Jan. 5, 1993

[54] USE OF CARBAZONES AS NOVEL ACTIVE INGREDIENTS IN MEDICAMENTS

[75] Inventors: Ulrich Feige, Riehen, Switzerland; Irmgard Wiesenberg, Weil am Rhein, Fed. Rep. of Germany; Leo Widler, Münchenstein, Switzerland; Pier G. Ferrini, Binningen, Switzerland; Martin Missbach, Rheinfelden, Switzerland

[73] Assignee: Ciba-Geigy Corporation, Ardsley, N.Y.

[21] Appl. No.: 795,210

[22] Filed: Nov. 20, 1991

[30] Foreign Application Priority Data

Dec. 6, 1990 [CH] Switzerland ............ 3868/90
Mar. 20, 1991 [CH] Switzerland ............ 844/91
Apr. 3, 1991 [CH] Switzerland ............ 986/91

[51] Int. Cl.$^5$ .................................. A61K 31/425
[52] U.S. Cl. .................................. 514/369
[58] Field of Search .......................... 514/369

[56] References Cited

U.S. PATENT DOCUMENTS 3,699,116 10/1972 Meisels et al. ............ 260/306.7
4,489,069 12/1984 Storni ...................... 260/306.7
4,582,841 4/1986 Storni ...................... 260/306.7
4,697,020 9/1987 Storni ...................... 260/306.7

FOREIGN PATENT DOCUMENTS 22515 1/1981 European Pat. Off.
1325061 8/1973 United Kingdom.

OTHER PUBLICATIONS

European Journal of Cancer, vol. 15, No. 5, 755–762 (May 1979) Jordan et al., "The Mode of Action of the Antitumour Agent GP4989 in the Pat."
Proc. Int. Cong. Chemother, vol. 16, 257/66–257/70 (1983), Schieweck et al., "CGP 19984A:Antitumour Activity in Vivo and in Vitro".
Merck Manual of Diagnosis and Therapy 15th Ed. (1987) pp. 1221–1228 and pp. 1239–1246.
Abstract of DE 2,632,747 (Feb. 1977).
Abstract of DE 2,632,746 (Feb. 1977).

*Primary Examiner*—S. J. Friedman
*Attorney, Agent, or Firm*—Irving M. Fishman; Karen G. Kaiser

[57] ABSTRACT

Compounds of formula I $$\underset{R_3}{\underset{|}{R_2-C}}\underset{S}{\overset{\displaystyle O}{\underset{\displaystyle \|}{C}}}\underset{}{\overset{R_1}{\underset{|}{N}}}\underset{}{C}=N-N=C\underset{S}{\overset{R_5}{\underset{|}{N}}}\underset{R_4}{\overset{\displaystyle O}{\underset{\displaystyle \|}{C}}} \quad (I)$$

wherein X and Y are each independently of the other thio or sulfynyl, $R_1$ is lower alk-2-en-1-yl, lower alk-3-en-2-yl, lower alk-2-yn-1-yl, or lower alkyl that is substituted in the 2,3-position by radicals that can be eliminated to form a double bond, $R_2$ is hydrogen and $R_3$ is unsubstituted methyl or methyl substituted by a radical that can be eliminated together with hydrogen Rhd 2 to form a double bond, or $R_2$ and $R_3$ are each hydrogen or lower alkyl or together are methylene, $R_4$ is free or protected hydroxy, or hydrogen, and $R_5$ is hydrogen, lower alkyl, lower alk-2-en-1-yl, lower alk-2-yn-1-yl, or lower alkyl that is substituted in the 2,3-position by radicals that can be eliminated to form a double bond, and their pharmaceutically acceptable salts may be used in a novel manner for the treatment of disorders of the rheumatoid type.

10 Claims, No Drawings

USE OF CARBAZONES AS NOVEL ACTIVE INGREDIENTS IN MEDICAMENTS

The invention relates to the use of carbazones of formula I

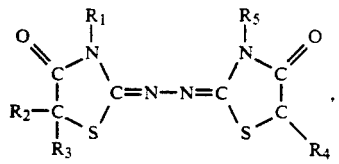

wherein X and Y are each independently of the other thio or sulfynyl, $R_1$ is lower alk-2-en-1-yl, lower alk-3-en-2-yl, lower alk-2-yn-1-yl, or lower alkyl that is substituted in the 2,3-position by radicals that can be eliminated to form a double bond, $R_2$ is hydrogen and $R_3$ is unsubstituted methyl or methyl substituted by a radical that can be eliminated together with hydrogen $R_2$ to form a double bond, or $R_2$ and $R_3$ are each hydrogen or lower alkyl or together are methylene, $R_4$ is free or protected hydroxy, or hydrogen, and $R_5$ is hydrogen, lower alkyl, lower alk-2-en-1-yl, lower alk-2-yn-1-yl, or lower alkyl that is substituted in the 2,3-position by radicals that can be eliminated to form a double bond, and their pharmaceutically acceptable salts, for the treatment of disorders of the rheumatoid type and for the preparation of pharmaceutical compositions therefor, to a method of treating disorders of the rheumatoid type, and to pharmaceutical compositions therefor comprising a compound of formula I or a pharmaceutically acceptable salt thereof together with customary pharmaceutical excipients.

Lower alkyl substituted in the 2,3-position by radicals that can be eliminated to form a double bond is, for example, 2- or 3-amino-, 2- or 3-lower alkylamino- or 2- or 3-di-lower alkylamino-lower alkyl, 2- or 3-lower alkyleneamino-, 2- or 3-(aza)-lower alkyleneamino-, 2- or 3-(oxa)-lower alkyleneamino- or 2- or 3-(thia)-lower alkyleneamino-lower alkyl, 2- or 3-hydroxy-, 2- or 3-lower alkanoyloxy-, 2- or 3-lower alkoxycarbonyloxy- or 2- or 3-tri-lower alkylsilyloxy-lower alkyl, or 2- or 3-halo-lower alkyl.

Methyl substituted by a radical that can be eliminated together with hydrogen $R_2$ to form a double bond is, for example, di-lower alkylaminoaminomethyl or halomethyl.

Protected hydroxy is, for example, lower alkanoyloxy, halo-lower alkanoyloxy, lower alkoxycarbonyloxy, benzoyloxy that is unsubstituted or substituted by lower alkyl, lower alkoxy, hydroxy, halogen and/or by nitro, sulfonyloxy, O-mono- or O,O-di-lower alkylphosphonyloxy or tri-lower alkylsilyloxy.

Throughout this specification, references to lower radicals and compounds shall be understood as meaning, for example, those having up to and including 7, preferably up to and including 4, carbon atoms (C-atoms).

Lower alkyl is, for example, $C_1$-$C_7$alkyl, preferably $C_1$-$C_4$alkyl, such as especially methyl or, secondly, ethyl, propyl, isopropyl or butyl, but may also be isobutyl, secondary butyl, tertiary butyl or a $C_5$-$C_7$alkyl group, such as a pentyl, hexyl or heptyl group.

Lower alkoxy is, for example, $C_1$-$C_7$alkoxy, preferably $C_1$-$C_4$alkoxy, such as methoxy, ethoxy, propoxy, isopropoxy or butoxy, but may also be isobutoxy, secondary butoxy, tertiary butoxy or a pentyloxy, hexyloxy or heptyloxy group.

Lower alk-2-en-1-yl is, for example, $C_3$-$C_7$alk-2-en-1-yl, especially $C_3$-$C_5$alk-2-en-1-yl, such as allyl (prop-2-en-1-yl) or methallyl (2-methylprop-2-en-1-yl). Lower alk-3-en-2-yl is, for example, $C_3$-$C_7$alk-3-en-2-yl, especially $C_3$-$C_5$alk-3-en-2-yl, such as but-3-en-2-yl.

Lower alk-2-ynyl is, for example, $C_3$-$C_7$alk-2-yn-1-yl, especially $C_3$-$C_5$alk-2-yn-1-yl, such as prop-2-yn-1-yl or 2-methylprop-2-yn-1-yl.

2- or 3-amino-lower alkyl is, for example, 2-amino-$C_3$-$C_7$alkyl, especially amino-$C_3$-$C_5$alkyl, such as 2-aminopropyl or 2-amino-2-methyl-propyl, or 3-amino-$C_3$-$C_7$alkyl, especially 3-amino-$C_3$-$C_5$alkyl, such as 3-aminopropyl or 3-amino-2-methyl-propyl.

2- or 3-lower alkylamino-lower alkyl is, for example, 2-$C_1$-$C_4$alkylamino-$C_3$-$C_7$alkyl, especially $C_1$-$C_4$alkylamino-$C_3$-$C_5$alkyl, such as 2-$C_1$-$C_4$alkylaminopropyl or 2-$C_1$-$C_4$alkylamino-2-methyl-propyl or 3-$C_1$-$C_4$alkylamino-$C_3$-$C_7$alkyl, especially 3-$C_1$-$C_4$alkylamino-$C_3$-$C_5$alkyl, such as 3-$C_1$-$C_4$alkylaminopropyl or 3-$C_1$-$C_4$alkylamino-2-methyl-propyl, wherein $C_1$-$C_4$alkyl is, for example, methyl, ethyl, propyl or butyl.

Di-lower alkylaminoaminomethyl is, for example, N,N-di-$C_1$-$C_4$alkylaminomethyl, such as N,N-dimethylaminomethyl, N,N-diethylaminomethyl, N-ethyl-N-methylaminomethyl, N,N-dipropylaminomethyl, N-methyl-N-propylaminomethyl, N-isopropyl-N-methylaminomethyl or N-butyl-N-methylaminomethyl, but may also be N-isobutyl-N-methylaminomethyl, N-methyl-N-secondary butylaminomethyl, N-methyl-N-tertiary butylaminomethyl or an N-methyl-N-pentylaminomethyl, N-hexyl-N-methylaminomethyl or N-heptyl-N-methylaminomethyl group.

2- or 3-di-lower alkylamino-lower alkyl is, for example, 2-(N,N-di-$C_1$-$C_4$alkylamino)-$C_3$-$C_7$alkyl, especially 2-(N,N-di-$C_1$-$C_4$alkylamino)-$C_3$-$C_5$alkyl, such as 2-(N,N-di-$C_1$-$C_4$alkylamino)propyl or 2-(N,N-di-$C_1$-$C_4$alkylamino)-2-methyl-propyl, or 3-(N,N-di-$C_1$-$C_4$alkylamino)-$C_3$-$C_7$alkyl, especially 3-(N,N-di-$C_1$-$C_4$alkylamino)-$C_3$-$C_5$alkyl, such as 3-(N,N-di-$C_1$-$C_4$alkylamino)propyl or 3-(N,N-di-$C_1$-$C_4$alkylamino)-2-methyl-propyl, wherein $C_1$-$C_4$alkyl is, for example, methyl, ethyl, propyl or butyl.

2- or 3-lower alkyleneamino-lower alkyl is, for example, 4- to 7-membered 2-(N,N-alkyleneamino)-$C_3$-$C_7$alkyl, especially 2-(N,N-alkyleneamino)-$C_3$-$C_5$alkyl, such as 2-(N,N-alkyleneamino)propyl or 2-(N,N-alkyleneamino)-2-methyl-propyl, or 3-(N,N-alkyleneamino)-$C_3$-$C_7$alkyl, especially 3-(N,N-alkyleneamino)-$C_3$-$C_5$alkyl, such as 3-(N,N-alkyleneamino)propyl or 3-(N,N-alkyleneamino)-2-methyl-propyl, wherein 4- to 7-membered N,N-alkyleneamino is especially pyrrolidino, piperidino or, secondly, hexahydroazepino or octahydroazocino.

2- or 3-(aza)-lower alkyleneamino-lower alkyl is, for example, 4- to 7-membered 2-[N,N-(aza)alkyleneamino]-$C_3$-$C_7$alkyl, especially 2-[N,N-(aza)alkyleneamino]-$C_3$-$C_5$alkyl, such as 2-[N,N-(aza)alkyleneamino]propyl or 2-[N,N-(aza)alkyleneamino]-2-methyl-propyl, or 3-[N,N-(aza)alkyleneamino]-$C_3$-$C_7$alkyl, especially 3-[N,N-(aza)alkyleneamino]-$C_3$-$C_5$alkyl, such as 3-[N,N-(aza)alkyleneamino]propyl or 3-[N,N-(aza)alkyleneamino]-2-methyl-propyl, wherein 4- to 7-membered N,N-(aza)alkyleneamino is especially piperazino or N'-$C_1$-$C_4$alkylpiperazino, such as N'- methylpiperazino, or N'-$C_1$-$C_7$alkanoylpiperazino, such as N'-acetyl- or N'-pivaloyl-piperazino.

2- or 3-(oxa)-lower alkyleneamino-lower alkyl is, for example, 4- to 7-membered 2-[N,N-(oxa)alkyleneamino]-$C_3$-$C_7$alkyl, especially 2-[N,N-(oxa)alkyleneamino]-$C_3$-$C_5$alkyl, such as 2-[N,N-(oxa)alkyleneamino]propyl or 2-[N,N-(oxa)alkyleneamino]-2-methylpropyl, or 3-[N,N-(oxa)alkyleneamino]-$C_3$-$C_7$alkyl, especially 3-[N,N-(oxa)alkyleneamino]-$C_3$-$C_5$alkyl, such as 3-[N,N-(oxa)alkyleneamino]propyl or 3-[N,N-(oxa)alkyleneamino]-2-methyl-propyl, wherein 4- to 7-membered N,N-(oxa)alkyleneamino is especially morpholino.

2- or 3-(thia)-lower alkyleneamino-lower alkyl is, for example, 4- to 7-membered unsubstituted or S-oxidised 2-[N,N-(thia)alkyleneamino]-$C_3$-$C_7$alkyl, especially 2-[N,N-(thia)alkyleneamino]-$C_3$-$C_5$alkyl, such as 2-[N,N-(thia)alkyleneamino]propyl or 2-[N,N-(thia)alkyleneamino]-2-methyl-propyl, or 3-[N,N-(thia)alkyleneamino]-$C_3$-$C_7$alkyl, especially 3-[N,N-(thia)alkyleneamino]-$C_3$-$C_5$alkyl, such as 3-[N,N-(thia)alkyleneamino]propyl or 3-[N,N-(thia)alkyleneamino]-2-methyl-propyl, wherein 4- to 7-membered unsubstituted or S-oxidised N,N-(thia)alkyleneamino is especially thiomorpholino or S-oxy- or S,S-dioxy-thiomorpholino.

2- or 3-hydroxy-lower alkyl is, for example, 2-hydroxy-$C_3$-$C_7$alkyl, especially 2-hydroxy-$C_3$-$C_5$alkyl, such as 2-hydroxypropyl or 2-hydroxy-2-methyl-propyl, or 3-hydroxy-$C_3$-$C_7$alkyl, especially 3-hydroxy-$C_3$-$C_5$alkyl, such as 3-hydroxypropyl or 3-hydroxy-2-methyl-propyl.

Lower alkanoyloxy is, for example, $C_1$-$C_7$alkanoyloxy, especially $C_1$-$C_5$alkanoyloxy, such as acetoxy, propionyloxy, butyryloxy, valeroyloxy or pivaloyloxy, but may also be $C_6$- or $C_7$-alkanoyloxy, such as caproyloxy.

2- or 3-lower alkanoyloxy-lower alkyl is, for example, 2-($C_1$-$C_7$alkanoyloxy)-$C_3$-$C_7$alkyl, especially 2-($C_1$-$C_7$alkanoyloxy)-$C_3$-$C_5$alkyl, such as 2-($C_1$-$C_7$alkanoyloxy)propyl or 2-($C_1$-$C_7$alkanoyloxy)-2-methyl-propyl, or 3-($C_1$-$C_7$alkanoyloxy)-$C_3$-$C_7$alkyl, especially 3-($C_1$-$C_7$alkanoyloxy)-$C_3$-$C_5$alkyl, such as 3-($C_1$-$C_7$alkanoyloxy)propyl or 3-($C_1$-$C_7$alkanoyloxy)-2-methyl-propyl, wherein $C_1$-$C_7$alkanoyloxy is especially $C_1$-$C_4$alkanoyloxy, such as acetoxy or pivaloyloxy.

Lower alkoxycarbonyloxy is, for example, $C_1$-$C_7$alkoxycarbonyloxy, preferably $C_1$-$C_4$alkoxycarbonyloxy, such as methoxycarbonyloxy, ethoxycarbonyloxy, propoxycarbonyloxy, isopropoxycarbonyloxy or butoxycarbonyloxy, but may also be isobutoxycarbonyloxy, secondary butoxycarbonyloxy, tertiary butoxycarbonyloxy or a pentyloxycarbonyloxy, hexyloxycarbonyloxy or heptyloxycarbonyloxy group.

2- or 3-lower alkoxycarbonyloxy-lower alkyl is, for example, 2-($C_1$-$C_7$alkoxycarbonyloxy)-$C_3$-$C_7$alkyl, especially 2-($C_1$-$C_7$alkoxycarbonyloxy)-$C_3$-$C_5$alkyl, such as 2-($C_1$-$C_7$alkoxycarbonyloxy)propyl or 2-($C_1$-$C_7$alkoxycarbonyloxy)-2-methyl-propyl, or 3-($C_1$-$C_7$alkoxycarbonyloxy)-$C_3$-$C_7$alkyl, especially 3-($C_1$-$C_7$alkoxycarbonyloxy)-$C_3$-$C_5$alkyl, such as 3-($C_1$-$C_7$alkoxycarbonyloxy)propyl or 3-($C_1$-$C_7$alkoxycarbonyloxy)-2-methyl-propyl, wherein $C_1$-$C_7$alkoxycarbonyloxy is especially $C_1$-$C_4$alkoxycarbonyloxy, such as tertiary butoxycarbonyloxy.

Tri-lower alkylsilyloxy is, for example, tri-$C_1$-$C_7$alkylsilyloxy, especially tri-$C_1$-$C_4$alkylsilyloxy, such as trimethylsilyloxy or tributylsilyloxy, or $C_4$-$C_7$alkyl(di-$C_1$-$C_4$alkyl)silyloxy, such as 1,2,2-trimethylpropyl(dimethyl)silyloxy.

2- or 3-tri-lower alkylsilyloxy-lower alkyl is, for example, 2-(tri-$C_1$-$C_7$alkylsilyloxy)-$C_3$-$C_7$alkyl, especially 2-(tri-$C_1$-$C_7$alkylsilyloxy)-$C_3$-$C_5$alkyl, such as 2-(tri-$C_1$-$C_7$alkylsilyloxy)propyl or 2-(tri-$C_1$-$C_7$alkylsilyloxy)-2-methyl-propyl, or 3-(tri-$C_1$-$C_7$alkylsilyloxy)-$C_3$-$C_7$alkyl, especially 3-(tri-$C_1$-$C_7$alkylsilyloxy)-$C_3$-$C_5$alkyl, such as 3-(tri-$C_1$-$C_7$alkylsilyloxy)propyl or 3-(tri-$C_1$-$C_7$alkylsilyloxy)-2-methyl-propyl, wherein tri-$C_1$-$C_7$alkylsilyloxy is especially tri-$C_1$-$C_4$alkylsilyloxy, such as trimethylsilyloxy or tributylsilyloxy, or $C_4$-$C_7$alkyl(di-$C_1$-$C_4$alkyl)silyloxy, such as 1,2,2-trimethylpropyl(dimethyl)silyloxy.

Halogen is, for example, halogen having an atomic number of up to and including 35, such as chlorine or fluorine, or also bromine.

2- or 3-halo-lower alkyl is, for example, 2-halo-$C_3$-$C_7$alkyl, especially 2-halo-$C_3$-$C_5$alkyl, such as 2-halopropyl or 2-halo-2-methyl-propyl, or 3-halo-$C_3$-$C_7$alkyl, especially 3-halo-$C_3$-$C_5$alkyl, such as 3-halopropyl or 3-halo-2-methyl-propyl, wherein $C_1$-$C_4$alkyl is, for example, halogen having an atomic number of up to and including 35, such as chlorine or fluorine, or also bromine.

Halomethyl is, for example, halomethyl wherein halo has an atomic number of up to and including 35 and is, for example, chlorine or fluorine, or also bromine.

Halo-lower alkanoyloxy is, for example, chloroacetoxy.

O-mono- or O,O-di-lower alkylphosphonyloxy is, for example, O-mono-$C_1$-$C_4$alkylphosphonyloxy, such as O-methyl- or O-ethyl-phosphonyloxy.

The compounds of formula I are basic, with the exception of those wherein $R_4$ is of an acidic nature which are therefore amphoteric. Basic compounds of formula I can form acid addition salts, and the mentioned amphoteric compounds of formula I can form salts with bases.

Pharmaceutically acceptable acid addition salts of compounds of formula I are, for example, pharmaceutically acceptable salts thereof with suitable mineral acids, such as hydrohalic acids, sulfuric acid or phosphoric acid, e.g. hydrochlorides, hydrobromides, sulfates, hydrogen sulfates or phosphates, salts with suitable aliphatic or aromatic sulfonic acids or N-substituted sulfamic acids, e.g. methanesulfonates, benzenesulfonates, p-toluenesulfonates or N-cyclohexylsulfamates (cyclamates), or salts with strong organic carboxylic acids, such as lower alkanecarboxylic acids or optionally unsaturated or hydroxylated aliphatic dicarboxylic acids, e.g. acetates, oxalates, malonates, maleates, fumarates, malates, tartrates or citronates.

Pharmaceutically acceptable salts of compounds of formula I with bases are, for example, salts thereof with pharmaceutically acceptable bases, such as non-toxic metal salts derived from metals of Groups Ia, Ib, IIa and IIb, e.g. alkali metal salts, especially sodium or potassium salts, alkaline earth metal salts, especially calcium or magnesium salts, and also ammonium salts with ammonia or organic amines or quaternary ammonium bases, such as unsubstituted or C-hydroxylated aliphatic amines, especially mono-, di- or tri-lower alkylamines, e.g. methyl-, ethyl- or diethyl-amine, mono-, di- or tri-(hydroxy-lower alkyl)amines, such as ethanol-, diethanol- or triethanol-amine, tris(hydroxymethyl)methylamine or 2-hydroxy-tertiary butylamine, or N-(hydroxy-lower alkyl)-N,N-di-lower alkylamines and N-

(polyhydroxy-lower alkyl)-N-lower alkylamines, such as 2-(dimethylamino)ethanol or D-glucamine, or quaternary aliphatic ammonium hydroxides, e.g. tetrabutylammonium hydroxide.

The compounds of formula I and processes for their preparation that are based on methods known per se are known and are described, for example, in GB-1 325 061, U.S. Pat. No. 4,697,020, DE-2 632 746, DE-2 632 747, EP-085 275 and EP-22 515. Novel compounds of formula I and their pharmaceutically acceptable salts can be prepared analogously to the methods described therein.

According to the mentioned specifications, the compounds of formula I and their pharmaceutically acceptable salts have tumour-inhibiting properties and have been proposed as tumour-inhibiting active ingredients in medicaments, especially for the treatment of neoplastic disorders in warm-blooded animals.

The present invention is based on the surprising discovery that, in addition to their known tumour-inhibiting activity, which is usually apparent at a daily dose ranging from approximately 10 to approximately 250 mg/kg i.p., the compounds of formula I and their pharmaceutically acceptable salts exhibit pronounced anti-arthritic properties at a very low dose which is below the tumour-inhibiting dose. These may be demonstrated in vivo, for example, in the rat adjuvant-arthritis model according to I. Wiesenberg et al. Clin. Exp. Immunol. 78, 245 (1989) at a dose ranging from approximately 0.1 to approximately 0.3 mg/kg p.o. or i.p..

The mechanism of the anti-arthritic activity of the compounds of formula I and their pharmaceutically acceptable salts is not yet precisely known. A direct immunosuppressive mechanism via lymphocytotoxicity or myelosuppression can, however, be ruled out, because even doses that are more than 100 times higher than the anti-arthritically effective dose do not result in the normally to be expected massive suppression of the lymphatic organs (thymus, spleen), or in leucopenia. Lymphocytotoxicity and myelosuppression are known undesired side effects in the treatment of rheumatoid disorders with cytostatics having immunosuppressive activity, e.g. with cyclophosphamide.

On the other hand, it has been possible to demonstrate that the compounds of formula I and their pharmaceutically acceptable salts inhibit the synthesis of the cytokine interleukin-1 in human monocytes. Interleukin-1 is an inflammation mediator which plays a key role in acute and chronic inflammatory processes. It must therefore be assumed that the compounds of formula I and their pharmaceutically acceptable salts possess properties that cause the anti-arthritic effects at doses that are lower than the cytostatically effective dose. A causative association with the said cytokine synthesis inhibition might exist, although other, as yet unknown immunomodulatory mechanisms cannot be excluded.

The compounds of formula I and their pharmaceutically acceptable salts can therefore be used for the treatment of disorders of the rheumatoid type according to the "preliminary proposal of the Glossary Committee of the American Rheumatism Association". Those disorders include especially rheumatoid arthritis, juvenile arthritis, ankylopoietic spondylitis and other seronegative spondylarthrites, e.g. spondylarthritis in the case of Colitis ulcerosa and Crohn's disease, but also reactive arthrites, collagen disorders, such as Lupus erythematosus, degenerative rheumatic disorders, extraarticular rheumatic and pararheumatic disorders, e.g. gout and osteoporosis.

The invention relates especially to the use of compounds of formula I wherein X and Y are each independently of the other thio or sulfynyl, $R_1$ is lower alk-2-en-1-yl, lower alk-3-en-2-yl, lower alk-2-yn-1-yl,2- or 2-amino-, 3-amino-, 2- or 3-lower alkylamino- or 2- or 3-di-lower alkylamino-lower alkyl, 2- or 3-lower alkyleneamino-, 2- or 3-(aza)-lower alkyleneamino-, 2- or 3-(oxa)-lower alkyleneamino- or 2- or 3-(thia)-lower alkyleneamino-lower alkyl, 2- or 3-hydroxy-, 2- or 3-lower alkanoyloxy-, 2- or 3-lower alkoxycarbonyloxy- or 2- or 3-tri-lower alkylsilyloxy-lower alkyl, or 2- or 3-halo-lower alkyl, $R_2$ is hydrogen and $R_3$ is hydrogen, lower alkyl, di-lower alkylaminoamino-lower alkyl or halomethyl, or $R_2$ and $R_3$ together are methylene, $R_4$ is hydroxy, lower alkanoyloxy, halo-lower alkanoyloxy, lower alkoxycarbonyloxy, benzoyloxy that is unsubstituted or substituted by lower alkyl, lower alkoxy, hydroxy, halogen and/or by nitro, sulfonyloxy, O-mono- or O,O-di-lower alkylphosphonyloxy, tri-lower alkylsilyloxy or hydrogen, and $R_5$ is hydrogen, lower alkyl, lower alk-2-en-1-yl, lower alk-2-yn-1-yl, 2- or 3-amino-, 2- or 3-lower alkylamino-or 2- or 3-di-lower alkylamino-lower alkyl, 2- or 3-lower alkyleneamino-, 2- or 3-(aza)-lower alkyleneamino-, 2- or 3-(oxa)-lower alkyleneamino- or 2- or 3-(thia)-lower alkyleneamino-lower alkyl, 2- or 3-hydroxy-, 2- or 3-lower alkanoyloxy-, 2- or 3-lower alkoxycarbonyloxy- or 2- or 3-silyloxy-lower alkyl, or 2- or 3-halo-lower alkyl, and their pharmaceutically acceptable salts, for the treatment of disorders of the rheumatoid type and for the preparation of pharmaceutical compositions therefor, to a method of treating disorders of the rheumatoid type, and to pharmaceutical compositions therefor comprising a compound of formula I or a pharmaceutically acceptable salt thereof together with customary pharmaceutical excipients.

The invention relates especially, for example, to the use of compounds of formula I wherein X and Y are each thio, $R_1$ is lower alk-2-en-1-yl, lower alk-3-en-2-yl, 2- or 3-amino-, 2- or 3-lower alkylamino- or 2- or 3-di-lower alkylamino-lower alkyl, 2- or 3-lower alkyleneamino-, 2- or 3-(aza)-lower alkyleneamino-, 2- or 3-(oxa)-lower alkyleneamino- or 2- or 3-(thia)-lower alkyleneamino-lower alkyl, 2- or 3-hydroxy-, 2- or 3-lower alkanoyloxy-, 2- or 3-lower alkoxycarbonyloxy- or 2- or 3-tri-lower alkylsilyloxy-lower alkyl, or 2- or 3-halo-lower alkyl, $R_2$ is hydrogen and $R_3$ is hydrogen, lower alkyl, di-lower alkylamino-lower alkyl or halomethyl, or $R_2$ and $R_3$ together are methylene, $R_4$ is hydroxy, lower alkanoyloxy, halo-lower alkanoyloxy, lower alkoxycarbonyloxy, benzoyloxy that is unsubstituted or substituted by lower alkyl, lower alkoxy, hydroxy, halogen and/or by nitro, sulfonyloxy, O-mono- or O,O-di-lower alkylphosphonyloxy, tri-lower alkylsilyloxy or hydrogen, and $R_5$ is hydrogen, lower alkyl, lower alk-2-en-1-yl, 2- or 3-amino-, 2- or 3-lower alkylamino- or 2- or 3-di-lower alkylamino-lower alkyl, 2- or 3-lower alkyleneamino-, 2- or 3-(aza)-lower alkyleneamino-, 2- or 3-(oxa)-lower alkyleneamino- or 2- or 3-(thia)-lower alkyleneamino-lower alkyl, 2- or 3-hydroxy-, 2- or 3-lower alkanoyloxy-, 2- or 3-lower alkoxycarbonyloxy- or 2- or 3-silyloxy-lower alkyl, or 2- or 3-halo-lower alkyl, and their pharmaceutically acceptable salts, for the treatment of disorders of the rheumatoid type and for the preparation of pharmaceutical compositions therefor, to a method of treating disorders of the rheumatoid type, and to pharmaceutical compositions therefor comprising a compound of formula I or a pharmaceutically acceptable salt thereof together with customary pharmaceutical excipients.

The invention relates more especially to the use of compounds of formula I wherein the radicals X and Y are each independently of the other thio or sulfynyl, $R_1$ is $C_3$–$C_7$alk-2-en-1-yl, such as allyl or methallyl, $C_3$–$C_7$alk-3-en-2-yl, such as but-3-en-2-yl, $C_3$–$C_7$alk-2-yn-1-yl, especially $C_3$–$C_5$alk-2-yn-1-yl, such as prop-2-yn-1-yl or 2-methylprop-2-yn-1-yl, or 2- or 3-halo-$C_3$–$C_7$alkyl, such as 2-bromoisobutyl, $R_2$ is hydrogen and $R_3$ is $C_1$–$C_4$alkyl, such as methyl, di-$C_1$–$C_4$alkylaminomethyl, such as dimethylaminomethyl, or halomethyl, such as 3-bromoisobutyl, or $R_2$ and $R_3$ are hydrogen or $C_1$–$C_4$alkyl, such as methyl, or together are methylene, $R_4$ is hydroxy, $C_1$–$C_7$alkanoyloxy, such as acetoxy or pivaloyloxy, benzoyloxy that is unsubstituted or substituted by $C_1$–$C_4$alkyl, such as methyl, $C_1$–$C_4$alkoxy, such as methoxy, hydroxy and/or by halogen, sulfonyloxy, O-$C_1$–$C_4$alkyl- or O,O-dialkylphosphonyloxy, such as O-methyl- or O,O-dimethylphosphonyloxy, tri-$C_1$–$C_7$alkylsilyloxy, such as trimethyl- or triisobutyl-silyloxy, or benzoyloxy that is unsubstituted or substituted by $C_1$–$C_4$alkyl, such as methyl, $C_1$–$C_4$alkoxy, such as methoxy, hydroxy and/or by halogen, and $R_5$ is hydrogen, $C_1$–$C_4$alkyl, such as methyl, $C_3$–$C_7$alk-2-en-1-yl, such as allyl or methallyl, $C_3$–$C_7$alk-2-yn-1-yl, especially $C_3$–$C_5$alk-2-yn-1-yl, such as prop-2-yn-1-yl or 2-methylprop-2-yn-1-yl, or 2- or 3-halo-$C_3$–$C_7$alkyl, such as 3-bromoisobutyl, and their pharmaceutically acceptable salts, for the treatment of disorders of the rheumatoid type and for the preparation of pharmaceutical compositions therefor, to a method of treating disorders of the rheumatoid type, and to pharmaceutical compositions therefor comprising a compound of formula I or a pharmaceutically acceptable salt thereof together with customary pharmaceutical excipients.

The invention relates preferably to the use of compounds of formula I wherein X and Y are each independently of the other thio or sulfynyl, $R_1$ is $C_3$–$C_7$alk-2-en-1-yl, such as allyl or methallyl, $C_3$–$C_7$alk-3-en-2-yl, such as but-3-en-2-yl, $C_3$–$C_7$alk-2-yn-1-yl, such as prop-2-yn-1-yl or 2-methylprop-2-yn-1-yl, or 2-halo-$C_3$–$C_7$alkyl, such as 2-bromoisobutyl, $R_2$ is hydrogen and $R_3$ is di-$C_1$–$C_4$alkylaminomethyl, such as dimethylaminomethyl, or $R_2$ and $R_3$ are each methyl or together are methylene, $R_4$ is hydroxy, $C_1$–$C_7$alkanoyloxy, such as acetoxy or pivaloyloxy, sulfonyloxy, O-$C_1$–$C_4$alkyl-phosphonyloxy, such as O-methylphosphonyloxy, tri-$C_1$–$C_4$alkylsilyloxy, such as trimethylsilyloxy or tributylsilyloxy, or $C_4$–$C_7$alkyl(di-$C_1$–$C_4$alkyl)silyloxy, such as 1,2,2-trimethylpropyl(dimethyl)silyloxy, and $R_5$ is $C_1$–$C_4$alkyl, such as methyl, $C_3$–$C_7$alk-2-yn-1-yl, such as prop-2-yn-1-yl or 2-methylprop-2-yn-1-yl, or $C_3$–$C_7$alk-2-en-1-yl, such as allyl or methallyl, and their pharmaceutically acceptable salts, for the treatment of disorders of the rheumatoid type and for the preparation of pharmaceutical compositions therefor, to a method of treating disorders of the rheumatoid type, and to pharmaceutical compositions therefor comprising a compound of formula I or a pharmaceutically acceptable salt thereof together with customary pharmaceutical excipients.

The invention relates preferably, for example, to the use of compounds of formula I wherein X and Y are each thio, $R_1$ is $C_3$–$C_7$alk-2-en-1-yl, such as allyl or methallyl, $C_3$–$C_7$alk-3-en-2-yl, such as but-3-en-2-yl, or 2-halo-$C_3$–$C_7$alkyl, such as 2-bromoisobutyl, $R_2$ is hydrogen and $R_3$ is di-$C_1$–$C_4$alkylaminomethyl, such as dimethylaminomethyl, or $R_2$ and $R_3$ are each methyl or together are methylene, $R_4$ is hydroxy, $C_1$–$C_7$alkanoyloxy, such as acetoxy or pivaloyloxy, sulfonyloxy, O-$C_1$–$C_4$alkylphosphonyloxy, such as O-methylphosphonyloxy, tri-$C_1$–$C_4$alkylsilyloxy, such as trimethylsilyloxy or tributylsilyloxy, or $C_4$–$C_7$alkyl(di-$C_1$–$C_4$alkyl)silyloxy, such as 1,2,2-trimethylpropyl(dimethyl)silyloxy, and $R_5$ is $C_1$–$C_4$alkyl, such as methyl, or $C_3$–$C_7$alk-2-en-1-yl, such as allyl or methallyl, and their pharmaceutically acceptable salts, for the treatment of disorders of the rheumatoid type and for the preparation of pharmaceutical compositions therefor, to a method of treating disorders of the rheumatoid type, and to pharmaceutical compositions therefor comprising a compound of formula I or a pharmaceutically acceptable salt thereof together with customary pharmaceutical excipients.

The invention relates especially to the use of compounds of formula I wherein X and Y are each independently of the other thio or sulfynyl, $R_1$ is $C_3$–$C_7$alk-2-en-1-yl, such as allyl or methallyl, $C_3$–$C_7$alk-2-yn-1-yl, such as prop-2-yn-1-yl or 2-methylprop-2-yn-1-yl, or 2-halo-$C_3$–$C_7$alkyl, such as 2-bromoisobutyl, $R_2$ is hydrogen or methyl, $R_3$ is methyl, $R_4$ is hydroxy, $C_1$–$C_7$alkanoyloxy, such as acetoxy or pivaloyloxy, sulfonyloxy, tri-$C_1$–$C_4$alkylsilyloxy, such as trimethylsilyloxy or tributylsilyloxy, or $C_4$–$C_7$alkyl(di-$C_1$–$C_4$alkyl)silyloxy, such as 1,2,2-trimethylpropyl(dimethyl)silyloxy, and $R_5$ is $C_1$–$C_4$alkyl, such as methyl, and their pharmaceutically acceptable salts, for the treatment of disorders of the rheumatoid type and for the preparation of pharmaceutical compositions therefor, to a method of treating disorders of the rheumatoid type, and to pharmaceutical compositions therefor comprising a compound of formula I or a pharmaceutically acceptable salt thereof together with customary pharmaceutical excipients.

The invention relates most especially to the use of compounds of formula I wherein X and Y are each independently of the other thio or sulfynyl, $R_1$ is $C_3$–$C_5$alk-2-en-1-yl, such as allyl or methallyl, $C_3$–$C_5$alk-2-yn-1-yl, such as prop-2-yn-1-yl or 2-methylprop-2-yn-1-yl, or 2-halo-$C_3$–$C_5$alkyl, such as 2-bromoisobutyl, $R_2$ is hydrogen and $R_3$ is di-$C_1$–$C_4$alkylaminomethyl, such as dimethylaminomethyl, or $R_2$ and $R_3$ together are methylene, $R_4$ is hydrogen and $R_5$ is $C_1$–$C_4$alkyl, such as methyl, and their pharmaceutically acceptable salts, for the treatment of disorders of the rheumatoid type and for the preparation of pharmaceutical compositions therefor, to a method of treating disorders of the rheumatoid type, and to pharmaceutical compositions therefor comprising a compound of formula I or a pharmaceutically acceptable salt thereof together with customary pharmaceutical excipients.

The invention relates most especially, for example, to the use of compounds of formula I wherein $R_1$ is $C_3$–$C_7$alk-2-en-1-yl, such as allyl or methallyl, or 2-halo-$C_3$–$C_7$alkyl, such as 2-bromoisobutyl, $R_2$ is hydrogen and $R_3$ is di-$C_1$–$C_4$alkylaminomethyl, such as dimethylaminomethyl, or $R_2$ and $R_3$ together are methylene, $R_4$ is hydrogen and $R_5$ is $C_1$–$C_4$alkyl, such as methyl, and their pharmaceutically acceptable salts, for the treatment of disorders of the rheumatoid type and for the preparation of pharmaceutical compositions therefor, to a method of treating disorders of the rheumatoid type, and to pharmaceutical compositions therefor comprising a compound of formula I or a pharmaceutically acceptable salt thereof together with customary pharmaceutical excipients.

The invention relates specifically to the use of 3-methallyl-2-(3-methyl-4-oxo-thiazolidin-2-ylidenehydrazono)-5-methylene-thiazolidin-4-one,
3-allyl-2-(3-methyl-4-oxo-thiazolidin-2-ylidenehydrazono)-5-methylene-thiazolidin-4-one,
3-methallyl-2-(3-methyl-4-oxo-thiazolidin-2-ylidenehydrazono)-5-dimethylaminomethyl-thiazolidin-4-one and its hydrochloride,
3-methallyl-2-(3-methyl-5-hydroxy-4-oxo-thiazolidin-2-ylidenehydrazono)-5-methyl-thiazolidin-4-one,
2-(5-acetoxy-3-methyl-4-oxo-thiazolidin-2-ylidenehydrazono)-3-methallyl-5-methyl-thiazolidin-4-one,
3-methallyl-2-(3-methyl-5-pivaloyloxy-4-oxo-thiazolidin-2-ylidenehydrazono)-5-methyl-thiazolidin-4-one,
3-methallyl-2-(3-methyl-5-sulfoxy-4-oxo-thiazolidin-2-ylidenehydrazono)-5-methyl-thiazolidin-4-one and its sodium salt,
methyl[3-methyl-2-(3-methallyl-5-methyl-4-oxo-thiazolidin-2-ylidenehydrazono)-4-oxo-thiazolidin-5-yl]phosphate, especially methyl[3-methyl-2-(3-methallyl-5(R*)-methyl-4-oxo-thiazolidin-2-ylidenehydrazono)-4-oxo-thiazolidin-5(R*)-yl]phosphate, and its sodium, potassium, ammonium, triethanolammonium, 2-hydroxyethylammonium or tertiary butylammonium salt,
3-methallyl-2-(3-methyl-5-trimethylsilyloxy-4-oxo-thiazolidin-2-ylidenehydrazono)-5,5-dimethyl-thiazolidin-4-one,
3-methallyl-2-(3-methyl-5-tributylsilyloxy-4-oxo-thiazolidin-2-ylidenehydrazono)-5-methyl-thiazolidin-4-one,
methyl[3-methyl-2-(3-allyl-4-oxo-thiazolidin-2-ylidenehydrazono)-4-oxo-thiazolidin-5-yl]phosphate and its sodium or tertiary butylammonium salt,
methyl[3-methyl-2-(3-allyl-5-methyl-4-oxo-thiazolidin-2-ylidenehydrazono)-4-oxo-thiazolidin-5-yl]phosphate and its sodium salt, A
3-methallyl-2-{3-methyl-5-[tertiary butyl(dimethyl)silyloxy]-4-oxo-thiazolidin-2-ylidenehydrazono}-5-methyl-thiazolidin-4-one,
methyl[3-methyl-2-(3-allyl-5,5-dimethyl-4-oxo-thiazolidin-2-ylidenehydrazono)-4-oxo-thiazolidin-5-yl]phosphate and its sodium salt,
3-methallyl-2-{3-methyl-5-[tertiary butyl(dimethyl)silyloxy]-4-oxo-thiazolidin-2-ylidenehydrazono}-5,5-dimethyl-thiazolidin-4-one,
3-methallyl-2-(3-methyl-5-triisopropylsilyloxy-4-oxo-thiazolidin-2-ylidenehydrazono)-5-methyl-thiazolidin-4-one,
3-methallyl-2-{3-methyl-5-[(2,3-dimethylbut-2-yl)(dimethyl)silyloxy]-4-oxo-thiazolidin-2-ylidenehydrazono}-5-methyl-thiazolidin-4-one,
5-hydroxymethyl-3-methallyl-2-(3-methyl-4-oxo-thiazolidin-2-ylidenehydrazono)-thiazolidin-4-one,
phosphoric acid dimethylamide-[3-methyl-2-(3-methallyl-5-methyl-4-oxo-thiazolidin-2-ylidenehydrazono)-4-oxo-thiazolidin-5-yl]ester,
[3-methyl-2-(3-methallyl-5-methyl-4-oxo-thiazolin-2-ylidenehydrazono)-5-thiazolidin-5-yloxy]-2-oxo-1,3,2-oxazaphospholidine,
3-methallyl-2-(4-oxo-thiazolidin-2-ylidenehydrazono)-thiazolidin-4-one,
3-methallyl-2-(1,4-dioxothiazolidin-2-ylidenehydrazono)-1-oxy-thiazolidin-4-one,
3-allyl-2-(3-methyl-5-hydroxy-4-oxo-thiazolidin-2-ylidenehydrazono)-thiazolidin-4-one,
3-methallyl-2-(3-allyl-5-hydroxy-4-oxo-thiazolidin-2-ylidenehydrazono)-5,5-dimethyl-thiazolidin-4-one,
3-(but-3-en-2-yl)-2-(4-oxo-thiazolidin-2-ylidenehydrazono)-thiazolidin-4-one,
3-methallyl-2-(3-methyl-4-oxo-thiazolidin-2-ylidenehydrazono)-5-methyl-thiazolidin-4-one,
3-allyl-2-(3-methyl-4-oxo-thiazolidin-2-ylidenehydrazono)-thiazolidin-4-one,
3-(but-3-en-2-yl)-2-(3-methyl-4-oxo-thiazolidin-2-ylidenehydrazono)-thiazolidin-4-one,
3-methallyl-2-(3-methyl-4-oxo-thiazolidin-2-ylidenehydrazono)-thiazolidin-4-one,
3-methallyl-2-(4-oxo-thiazolidin-2-ylidenehydrazono)-thiazolidin-4-one,
3-methallyl-2-(3-allyl-4-oxo-thiazolidin-2-ylidenehydrazono)-5,5-dimethyl-1-oxo-thiazolidin-4-one,
3-allyl-2-(3-methyl-4-oxo-thiazolidin-2-ylidenehydrazono)-1-oxo-thiazolidin-4-one,
3-methallyl-2-(3-allyl-1,4-dioxo-thiazolidin-2-ylidenehydrazono)-5,5-dimethyl-1-oxo-thiazolidin-4-one,
3-allyl-2-(3-methyl-1,4-dioxo-thiazolidin-2-ylidenehydrazono)-thiazolidin-4-one,
dimethyl[3-methyl-2-(3-methallyl-5-methyl-4-oxo-thiazolidin-2-ylidenehydrazono)-4-oxo-thiazolidin-5-yl]phosphate and
3-(prop-2-ynyl-2-(3-methyl-4-oxo-thiazolidin-2-ylidenehydrazono)-thiazolidin-4-one for the treatment of disorders of the rheumatoid type and for the preparation of pharmaceutical compositions therefor, to a method of treating disorders of the rheumatoid type, and to pharmaceutical compositions therefor comprising a compound of formula I or a pharmaceutically acceptable salt thereof together with customary pharmaceutical excipients.

The compounds of formula I and their pharmaceutically acceptable salts are preferably used in the form of, or for the preparation of, pharmaceutical compositions.

The pharmaceutical compositions according to the invention that comprise a compound according to the invention or a pharmaceutically acceptable salt thereof are for enteral, such as oral, or also rectal, and parenteral administration to warm-blooded animals. The compositions comprise the pharmacological active ingredient on its own or together with a pharmaceutically acceptable carrier. The daily dose of the active ingredient depends upon the age and the individual condition, and also upon the mode of administration.

The novel pharmaceutical compositions comprise e.g. from approximately 10% to approximately 80%, preferably from approximately 20% to approximately 60%, active ingredient. Pharmaceutical compositions according to the invention for enteral and parenteral administration are e.g. in unit dose form, such as dragées, tablets, capsules or suppositories, and also ampoules. They are prepared in a manner known per se, e.g. by means of conventional mixing, granulating, confectioning, dissolving or lyophilising processes. For example, pharmaceutical compositions for oral administration can be obtained by combining the active ingredient with solid carriers, if desired granulating a resulting mixture, and processing the mixture or granules, if desired or necessary, after the addition of appropriate excipients, into tablets or dragée cores.

Suitable carriers are especially fillers, such as sugars, e.g. lactose, saccharose, mannitol or sorbitol, cellulose preparations and/or calcium phosphates, e.g. tricalcium phosphate or calcium hydrogen phosphate, and binders, such as starch pastes using e.g. corn, wheat, rice or potato starch, gelatin, tragacanth, methylcellulose and/or polyvinylpyrrolidone, and, if desired, disintegrators, such as the above-mentioned starches, also carboxymethyl starch, crosslinked polyvinylpyrrolidone, agar, alginic acid or a salt thereof, such as sodium alginate. Excipients are especially flow conditioners and lubricants, e.g. silicic acid, talc, stearic acid or salts thereof, such as magnesium or calcium stearate, and/or polyethylene glycol. Dragée cores are provided with suitable, optionally enteric, coatings, there being used, inter alia, concentrated sugar solutions which may comprise gum arabic, talc, polyvinylpyrrolidone, polyethylene glycol and/or titanium dioxide, or coating solutions in suitable organic solvents or solvent mixtures, or, for the preparation of enteric coatings, solutions of suitable cellulose preparations, such as acetylcellulose phthalate or hydroxypropylmethylcellulose phthalate. Dyes or pigments may be added to the tablets or dragée coatings, e.g. for identification purposes or to indicate different doses of active ingredient.

Other orally administrable pharmaceutical compositions are dry-filled capsules consisting of gelatin, and also soft sealed capsules consisting of gelatin and a plasticiser, such as glycerol or sorbitol. The dry-filled capsules may contain the active ingredient in the form of granules, for example in admixture with fillers, such as lactose, binders, such as starches, and/or glidants, such as talc or magnesium stearate, and, if desired, stabilisers. In soft capsules, the active ingredient is preferably dissolved or suspended in suitable liquids, such as fatty oils, paraffin oil or liquid polyethylene glycol, to which stabilisers may also be added.

Suitable rectally administrable pharmaceutical compositions are e.g. suppositories that consist of a combination of the active ingredient with a suppository base. Suitable suppository bases are e.g. natural or synthetic triglycerides, paraffin hydrocarbons, polyethylene glycol or higher alkanols. It is also possible to use gelatin rectal capsules, which contain a combination of the active ingredient with a base material. Suitable base materials are e.g. liquid triglycerides, polyethylene glycol or paraffin hydrocarbons.

For parenteral administration there are suitable, especially, aqueous solutions of an active ingredient in water-soluble form, e.g. in the form of a water-soluble salt, or also suspensions of the active ingredient, such as corresponding oily injection suspensions, there being used suitable lipophilic solvents or vehicles, such as fatty oils, e.g. sesame oil, or synthetic fatty acid esters, e.g. ethyl oleate or triglycerides, or aqueous injection suspensions that comprise viscosity-increasing substances, e.g. sodium carboxymethylcellulose, sorbitol and/or dextran, and, if desired, also stabilisers.

The dose of the active ingredient depends upon the species of warm-blooded animal, the age and the individual condition, and upon the mode of administration. Normally, for a patient weighing approximately 75 kg, the estimated approximate daily dose for oral admistration is from approximately 5 mg to approximately 1000 mg, especially from approximately 10 mg to approximately 200 mg. This can be administered in a single dose or can be divided into several, for example from 2 to 4, individual doses. Pharmaceutical compositions in unit dose form therefore comprise from approximately 5 mg to approximately 250 mg, especially from approximately 10 mg to approximately 50 mg, of active ingredient.

The following Examples serve to illustrate the invention, but are not intended to limit the scope thereof in any way.

EXAMPLE 1

Tablets, each comprising 10 mg of 3-allyl-2-(3-methyl-4-oxo-thiazolidin-2-ylidenehydrazono)-thiazolidin-4-one or a salt thereof, may be prepared as follows:

| Composition (10000 tablets): | |
|---|---|
| active ingredient | 100.0 g |
| lactose | 450.0 g |
| potato starch | 350.0 g |
| gelatin | 10.0 g |
| talc | 60.0 g |
| magnesium stearate | 10.0 g |
| silica (highly dispersed) | 20.0 g |
| ethanol | q.s. |

The active ingredient is mixed with the lactose and 292 g of potato starch, and the mixture is moistened with an ethanolic solution of the gelatin and granulated through a sieve. After drying, the remainder of the potato starch, the magnesium stearate, the talc and the silica are admixed and the mixture is compressed to form tablets, each weighing 100.0 mg and comprising 50.0 mg of active ingredient, which, if desired, may be provided with dividing notches for finer adjustment of the dose.

EXAMPLE 2

Gelatin dry-filled capsules each comprising 20 mg of active ingredient, e.g. 3-allyl-2-(3-methyl-4-oxo-thiazolidin-2-ylidenehydrazono)-thiazolidin-4-one or a salt thereof, may be prepared e.g. as follows:

| Composition (for 1000 capsules): | |
|---|---|
| active ingredient | 20.0 g |
| lactose | 240.0 g |
| microcrystalline cellulose | 30.0 g |
| sodium lauryl sulfate | 2.0 g |
| magnesium stearate | 8.0 g |

The sodium lauryl sulfate is added to the lyophilised active ingredient through a sieve of 0.2 mm mesh size. The two components are homogeneously mixed. Then first the lactose is added through a sieve of 0.6 mm mesh size and subsequently the microcrystalline cellulose is added through a sieve of 0.9 mm mesh size. The mixture is then again homogeneously mixed for 10 minutes. Finally, the magnesium stearate is added through a sieve of 0.8 mm mesh size. After further mixing for 3 minutes, size 0 gelatin dry-fill capsules are each filled with 300 mg of the resulting formulation.

EXAMPLE 3

Gelatin dry-filled capsules each comprising 100 mg of active ingredient, e.g. 3-allyl-2-(3-methyl-4-oxo-thiazolidin-2-ylidenehydrazono)-thiazolidin-4-one or a salt thereof, may be prepared e.g. as follows:

| Composition (for 1000 capsules): | |
| --- | --- |
| active ingredient | 100.0 g |
| lactose | 250.0 g |
| microcrystalline cellulose | 30.0 g |
| sodium lauryl sulfate | 2.0 g |
| magnesium stearate | 8.0 g |

The sodium lauryl sulfate is added to the lyophilised active ingredient through a sieve of 0.2 mm mesh size. The two components are homogeneously mixed. Then first the lactose is added through a sieve of 0.6 mm mesh size and subsequently the microcrystalline cellulose is added through a sieve of 0.9 mm mesh size. The mixture is then again homogeneously mixed for 10 minutes. Finally, the magnesium stearate is added through a sieve of 0.8 mm mesh size. After further mixing for 3 minutes, size 0 gelatin dry-fill capsules are each filled with 390 mg of the resulting formulation.

EXAMPLE 4

Film-coated tablets, each comprising 50 mg of 3-allyl-2-(3-methyl-4-oxo-thiazolidin-2-ylidenehydrazono)-thiazolidin-4-one or a salt thereof, may be prepared as follows:

| Composition (for 1000 film-coated tablets): | |
| --- | --- |
| active ingredient | 50.00 g |
| lactose | 100.00 g |
| corn starch | 70.00 g |
| talc | 10.00 g |
| calcium stearate | 2.00 g |
| hydroxypropylmethylcellulose | 2.36 g |
| shellac | 0.64 g |
| water | q.s. |
| methylene chloride | q.s. |

The active ingredient, the lactose and 40 g of the corn starch are mixed together, moistened with a paste prepared from 15 g of corn starch and water (with heating), and granulated. The granules are dried, and the remainder of the corn starch, the talc and the calcium stearate are added and mixed with the granules. The mixture is compressed into tablets (each weighing 240 mg) and these are film-coated with a solution of the hydroxypropylmethylcellulose and the shellac in methylene chloride; final weight of each film-coated tablet: 283 mg.

EXAMPLE 5

A 0.2% injection or infusion solution of 3-allyl-2-(3-methyl-4-oxo-thiazolidin-2-ylidenehydrazono)-thiazolidin-4-one or of a salt thereof may be prepared e.g. as follows:

| Composition (for 1000 ampoules) | |
| --- | --- |
| active ingredient | 5.0 g |
| sodium chloride | 22.5 g |
| phosphate buffer pH = 7.4 | 300.0 g |
| demineralised water | ad 2500.0 ml |

The active ingredient and the sodium chloride are dissolved in 1000 ml of water and filtered through a microfilter. The buffer solution is added, and the resulting mixture is made up to 2500 ml with water. To produce unit dose forms, 1.0 or 2.5 ml portions are introduced into each glass ampoule, which then contains 2.0 or 5.0 mg of active ingredient respectively.

EXAMPLE 6

A 1% ointment (O/W emulsion) comprising as active ingredient e.g. 3-allyl-2-(3-methyl-4-oxo-thiazolidin-2-ylidenehydrazono)-thiazolidin-4-one or a salt thereof

| Composition: | |
| --- | --- |
| active ingredient | 1.0 g |
| cetyl alcohol | 3.0 g |
| glycerol | 6.0 g |
| methylparaben | 0.18 g |
| propylparaben | 0.05 g |
| Arlacel 60 | 0.6 g |
| Tween 60 | 4.4 g |
| stearic acid | 9.0 g |
| isopropyl palmitate | 2.0 g |
| viscous paraffin oil | 10.0 g |
| demineralised water q.s. ad | 100.0 g |

EXAMPLE 7

A 1% gel comprising as active ingredient e.g. 3-allyl-2-(3-methyl-4-oxo-thiazolidin-2-ylidenehydrazono)-thiazolidin-4-one or a salt thereof

| Composition: | |
| --- | --- |
| active ingredient | 1.0 g |
| Carbopol 934P | 1.0 g |
| glycerol | 3.0 g |
| isopropanol | 25.0 g |
| Softigen 767 | 0.2 g |
| demineralised water q.s. ad | 100.0 g |

EXAMPLE 8

In a manner analogous to those described in the preceding Examples 1 to 7 it is alos possible to prepare pharmaceutical compositions comprising 3-methallyl-2-(3-methyl-4-oxo-thiazolidin-2-ylidenehydrazono)-5-methylene-thiazolidin-4-one, 3-methallyl-2-(3-methyl-4-oxo-thiazolidin-2-yilidenehydrazono)-5-dimethylaminomethyl-thiazolidin-4-one or its hydrochloride, 3-methallyl-2-(3-methyl-5-hydroxy-4-oxo-thiazolidin-2-ylidenehydrazono)-5-methyl-thiazolidin-4-one, 2-(5-acetoxy-3-methyl-4-oxo-thiazolidin-2-ylidenehydrazono)-3-methallyl-5-methyl-thiazolidin-4-one, 3-methallyl-2-(3-methyl-5-pivaloyloxy-4-oxo-thiazolidin-2-ylidenehydrazono)-5-methyl-thiazolidin-4-one, 3-methallyl-2-(3-methyl-5-sulfoxy-4-oxo-thiazolidin-2-ylidenehydrazono)-5-methyl-thiazolidin-4-one or its sodium salt, methyl[3-methyl-2-(3-methallyl-5-methyl-4-oxo-thiazolidin-2-ylidenehydrazono)-4-oxo-thiazolidin-5-yl]phosphate, especially methyl[3-methyl-2-(3-methallyl-5(R*)-methyl-4-oxo-thiazolidin-2-ylidenehydrazono)-4-oxo-thiazolidin-5(R*)-yl]phosphate, or its sodium, potassium, ammonium, triethanolammonium, 2-hydroxyethylammonium or tertiary butylammonium salt, 3-methallyl-2-(3-methyl-5-trimethylsilyloxy-4-oxo-thiazolidin-2-ylidenehydrazono)-5,5-dimethyl-thiazolidin-4-one, 3-methallyl-2-(3-methyl-5-tributylsilyloxy-4-oxo-thiazolidin-2-ylidenehydrazono)-5-methyl-thiazolidin-4-one, methyl[3-methyl-2-(3-allyl-4-oxo-thiazolidin-2-ylidenehydrazono)-4-oxo-thiazolidin-5-yl]phosphate or its sodium or tertiary butylammonium salt, methyl[3-methyl-2-(3-allyl-5-methyl-4-oxo-thiazolidin-2-ylidenehydrazono)-4-oxo-thiazolidin-5-yl]phosphate or its sodium salt, 3-methallyl-2-{3-methyl-5-[tertiary butyl(dimethyl)silyloxy]-4-oxo-thiazolidin-2-ylidenehydrazono}-5-methyl-thiazolidin-4-one, methyl[3-methyl-2-(3-allyl-5,5-dimethyl-4-oxo-thiazolidin-2-ylidenehydrazono)-4-oxo-thiazolidin-5-yl]phosphate or its sodium salt, 3-methallyl-2-{3-methyl-5-[tertiary butyl(dimethyl)silyloxy]-4-oxo-thiazolidin-2-ylidenehydrazono}-5,5-dimethyl-thiazolidin-4-one, 3-methallyl-2-(3-methyl-5-triisopropylsilyloxy-4-oxo-thiazolidin-2-ylidenehydrazono)-5-methyl-thiazolidin-4-one, 3-methallyl-2-{3-methyl-5-[(2,3-dimethylbut-2-yl)(dimethyl)silyloxy]-4-oxo-thiazolidin-2-ylidenehydrazono}-5-methyl-thiazolidin-4-one, 5-hydroxymethyl-3-methallyl-2-(3-methyl-4-oxo-thiazolidin-2-ylidenehydrazono)-thiazolidin-4-one, phosphoric acid dimethylamide-[3-methyl-2-(3-methallyl-5-methyl-4-oxo-thiazolidin-2-ylidenehydrazono)-4-oxo-thiazolidin-5-yl]ester,

[3-methyl-2-(3-methallyl-5-methyl-4-oxo-thiazolidin-2-ylidenehydrazono)-5-thiazolidin-5-yloxy]-2-oxo-1,3,2-oxazapholidine, 3-methallyl-2-(4-oxo-thiazolidin-2-ylidenehydrazono)-thiazolidin-4-one, 3-allyl-2-(3-methyl-5-hydroxy-4-oxo-thiazolidin-2-ylidenehydrazono)-thiazolidin-4-one, 3-methallyl-2-(3-allyl-5-hydroxy-4-oxo-thiazolidin-2-ylidenehydrazono)-5,5-dimethyl-thiazolidin-4-one, 3-(but-3-en-2-yl)-2-(4-oxo-thiazolidin-2-ylidenehydrazono)-thiazolidin-4-one, 3-methallyl-2-(3-methyl-4-oxo-thiazolidin-2-ylidenehydrazono)-5-methyl-thiazolidin-4-one, 3-allyl-2-(3-methyl-4-oxo-thiazolidin-2-ylidenehydrazono)-thiazolidin-4-one, 3-(but-3-en-2-yl)-2-(3-methyl-4-oxo-thiazolidin-2-ylidenehydrazono)-thiazolidin-4-one, 3-methallyl-2-(3-methyl-4-oxo-thiazolidin-2-ylidenehydrazono)-thiazolidin-4-one, 3-methallyl-2-(4-oxo-thiazolidin-2-ylidenehydrazono)-thiazolidin-4-one, 3-methallyl-2-(1,4-dioxothiazolidin-2-ylidenehydrazono)-1-oxy-thiazolidin-4-one, 3-methallyl-2-(1,4-dioxothiazolidin-2-ylidenehydrazono)-1-oxy-thiazolidin-4-one, 3-methallyl-2-(3-allyl-4-oxo-thiazolidin-2-ylidenehydrazono)-5,5-dimethyl-1-oxo-thiazolidin-4-one, 3-allyl-2-(3-methyl-4-oxo-thiazolidin-2-ylidenehydrazono)-1-oxo-thiazolidin-4-one, 3-methallyl-2-(3-allyl-1,4-dioxo-thiazolidin-2-ylidenehydrazono)-5,5-dimethyl-1-oxo-thiazolidin-4-one, 3-allyl-2-(3-methyl-1,4-dioxo-thiazolidin-2-ylidenehydrazonon)-thiazolidin-4-one, dimethyl[3-methyl-2-(3-methallyl-5-methyl-4-oxo-thiazolidin-2-ylidenehydrazono)-4-oxo-thiazolidin-5-yl]phosphate or 3-(prop-2-ynyl-2-(3-methyl-4-oxo-thiazolidin-2-ylidenehydrazono)-thiazolidin-4-one.

What is claimed is:

1. A method of treating disorders of the rheumatoid type, which comprises administering to a warm-blooded organism requiring treatment a therapeutically effective amount of a compound of formula I

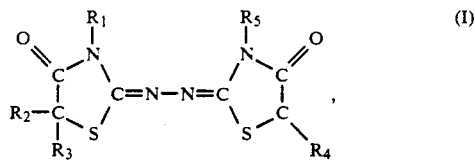

wherein X and Y are each independently of the other thio or sulfynyl, $R_1$ is lower alk-2-en-1-yl, lower alk-3-en-2-yl, lower alk-2-yn-1-yl, or lower alkyl that is substituted in the 2,3-position by radicals that can be eliminated to form a double bond, $R_2$ is hydrogen and $R_3$ is unsubstituted methyl or methyl substituted by a radical that can be eliminated together with hydrogen $R_2$ to form a double bond, or $R_2$ and $R_3$ are each hydrogen or lower alkyl or together are methylene, $R_4$ is free or protected hydroxy, or hydrogen, and $R_5$ is hydrogen, lower alkyl, lower alk-2-en-1-yl, lower alk-2-yn-1-yl, or lower alkyl that is substituted in the 2,3-position by radicals that can be eliminated to form a double bond, or a pharmaceutically acceptable salt thereof.

2. A method of treatment according to claim 1, wherein there is selected a compound of formula I wherein X and Y are each independently of the other thio or sulfynyl, $R_1$ is lower alk-2-en-1-yl, lower alk-3-en-2-yl, lower alk-2-yn-1-yl, 2- or 3-amino-, 2- or 3-lower alkylamino- or 2- or 3-di-lower alkylamino-lower alkyl, 2- or 3-lower alkyleneamino-, 2- or 3-(aza)-lower alkyleneamino-, 2- or 3-(oxa)-lower alkyleneamino- or 2- or 3-(thia)-lower alkyleneamino-lower alkyl, 2- or 3-hydroxy-, 2- or 3-lower alkanoyloxy-, 2- or 3-lower alkoxycarbonyloxy- or 2- or 3-tri-lower alkylsilyloxy-lower alkyl, or 2- or 3-halo-lower alkyl, $R_2$ is hydrogen and $R_3$ is hydrogen, lower alkyl, di-lower alkylamino-lower alkyl or halomethyl, or $R_2$ and $R_3$ together are methylene, $R_4$ is hydroxy, lower alkanoyloxy, halo-lower alkanoyloxy, lower alkoxycarbonyloxy, benzoyloxy that is unsubstituted or substituted by lower alkyl, lower alkoxy, hydroxy, halogen and/or by nitro, sulfonyloxy, O-mono- or O,O-di-lower alkylphosphonyloxy, tri-lower alkylsilyloxy or hydrogen, and $R_5$ is hydrogen, lower alkyl, lower alk-2-en-1-yl, lower alk-2-yn-1-yl, 2- or 3-amino-, 2- or 3-lower alkylamino- or 2- or 3-di-lower alkylamino-lower alkyl, 2- or 3-lower alkyleneamino-, 2- or 3-(aza)-lower alkyleneamino-, 2- or 3-(oxa)-lower alkyleneamino- or 2- or 3-(thia)-lower alkyleneamino-lower alkyl, 2- or 3-hydroxy-, 2- or 3-lower alkanoyloxy-, 2- or 3-lower alkoxycarbonyloxy- or 2- or 3-silyloxy-lower alkyl, or 2- or 3-halo-lower alkyl, or a pharmaceutically acceptable salt thereof.

3. A method of treatment according to claim 1, wherein there is selected a compound of formula I wherein X and Y are each thio, $R_1$ is lower alk-2-en-1-yl, lower alk-3-en-2-yl, 2- or 3-amino-, 2- or 3-lower alkylamino- or 2- or 3-di-lower alkylamino-lower alkyl, 2- or 3-lower alkyleneamino-, 2- or 3-(aza)-lower alkyleneamino-, 2- or 3-(oxa)-lower alkyleneamino- or 2- or 3-(thia)-lower alkyleneamino-lower alkyl, 2- or 3-hydroxy-, 2- or 3-lower alkanoyloxy-, 2- or 3-lower alkoxycarbonyloxy- or 2- or 3-tri-lower alkylsilyloxy-lower alkyl, or 2- or 3-halo-lower alkyl, $R_2$ is hydrogen and $R_3$ is hydrogen, lower alkyl, di-lower alkylamino-lower alkyl or halomethyl, or $R_2$ and $R_3$ together are methylene, $R_4$ is hydroxy, lower alkanoyloxy, halo-lower alkanoyloxy, lower alkoxycarbonyloxy, benzoyloxy that is unsubstituted or substituted by lower alkyl, lower alkoxy, hydroxy, halogen and/or by nitro, sulfonyloxy, O-mono- or O,O-di-lower alkylphosphonyloxy, tri-lower alkylsilyloxy or hydrogen, and $R_5$ is hydrogen, lower alkyl, lower alk-2-en-1-yl, 2- or 3-amino-, 2- or 3-lower alkylamino- or 2- or 3-di-lower alkylamino-lower alkyl, 2- or 3-lower alkyleneamino-, 2- or 3-(aza)-lower alkyleneamino-, 2- or 3-(oxa)-lower alkyleneamino-or 2- or 3-(thia)-lower alkyleneamino-lower alkyl, 2- or 3-hydroxy-, 2- or 3-lower alkanoyloxy-, 2- or 3-lower alkoxycarbonyloxy- or 2- or 3-silyloxy-lower alkyl, or 2- or 3-halo-lower alkyl, or a pharmaceutically acceptable salt thereof.

4. A method of treatment according to claim 1, wherein there is selected a compound of formula I wherein X and Y are each independently of the other thio or sulfynyl, $R_1$ is $C_3$–$C_7$alk-2-en-1-yl, $C_3$–$C_7$alk-3-en-2-yl, $C_3$–$C_7$alk-2-yn-1-yl or 2- or 3-halo-$C_3$–$C_7$alkyl, $R_2$ is hydrogen and $R_3$ is $C_1$–$C_4$alkyl, di-$C_1$–$C_4$alkylaminomethyl or halomethyl, or $R_2$ and $R_3$ are hydrogen or $C_1$–$C_4$alkyl or together are methylene, $R_4$ is hydroxy, $C_1$–$C_7$alkanoyloxy, benzoyloxy that is unsubstituted or substituted by $C_1$–$C_4$alkyl, $C_1$–$C_4$alkoxy, hydroxy and/or by halogen, sulfonyloxy, O-$C_1$–$C_4$alkyl- or O,O-di-$C_1$–$C_4$alkyl-phosphonyloxy, tri-$C_1$–$C_7$alkylsilyloxy, or benzoyloxy that is unsubstituted or substituted by $C_1$–$C_4$alkyl, $C_1$–$C_4$alkoxy, hydroxy and/or by halogen, and $R_5$ is hydrogen, $C_1$–$C_4$alkyl, $C_3$–$C_7$alk-2-en-1-yl, $C_3$–$C_7$alk-2-yn-1-yl or 2- or 3-halo-$C_3$–$C_7$alkyl, or a pharmaceutically acceptable salt thereof.

5. A method of treatment according to claim 1, wherein there is selected a compound of formula I wherein X and Y are each independently of the other thio or sulfynyl, $R_1$ is $C_3$–$C_7$alk-2-en-1-yl, $C_3$–$C_7$alk-3-en-2-yl, $C_3$–$C_7$alk-2-yn-1-yl or 2-halo-$C_3$–$C_7$alkyl, $R_2$ is hydrogen and $R_3$ is di-$C_1$–$C_4$alkylaminomethyl, or $R_2$ and $R_3$ are each methyl or together are methylene, $R_4$ is hydroxy, $C_1$–$C_7$alkanoyloxy, sulfonyloxy, O-$C_1$–$C_4$alkylphosphonyloxy, tri-$C_1$–$C_4$alkylsilyloxy or $C_4$–$C_7$alkyl(di-$C_1$–$C_4$alkyl)silyloxy, and $R_5$ is $C_1$–$C_4$alkyl, $C_3$–$C_7$alk-2-yn-1-yl or $C_3$–$C_7$alk-2-en-1-yl, or a pharmaceutically acceptable salt thereof.

6. A method of treatment according to claim 1, wherein there is selected a compound of formula I wherein X and Y are each thio, $R_1$ is $C_3$–$C_7$alk-2-en-1-yl, $C_3$–$C_7$alk-3-en-2-yl or 2-halo-$C_3$–$C_7$alkyl, $R_2$ is hydrogen and $R_3$ is di-$C_1$–$C_4$alkylaminomethyl, or $R_2$ and $R_3$ are each methyl or together are methylene, $R_4$ is hydroxy, $C_1$–$C_7$alkanoyloxy, sulfonyloxy, O-$C_1$–$C_4$alkylphosphonyloxy, tri-$C_1$–$C_4$alkylsilyoxy or $C_4$–$C_7$alkyl(di-$C_1$–$C_4$alkyl)silyloxy, and $R_5$ is $C_1$–$C_4$alkyl or $C_3$–$C_7$alk-2-en-1-yl, or a pharmaceutically acceptable salt thereof.

7. A method of treatment according to claim 1, wherein there is selected a compound of formula I wherein X and Y are each independently of the other thio or sulfynyl, $R_1$ is $C_3$–$C_7$alk-2-en-1-yl, $C_3$–$C_7$alk-2-yn-1-yl or 2-halo-$C_3$–$C_7$alkyl, $R_2$ is hydrogen or methyl, $R_3$ is methyl, $R_4$ is hydroxy, $C_1$–$C_7$alkanoyloxy, sulfonyloxy, tri-$C_1$–$C_4$alkylsilyloxy or $C_4$–$C_7$alkyl(di-$C_1$–$C_4$alkyl)silyloxy, and $R_5$ is $C_1$–$C_4$alkyl, or a pharmaceutically acceptable salt thereof.

8. A method of treatment according to claim 1, wherein there is selected a compound of formula I wherein X and Y are each independently of the other thio or sulfynyl, $R_1$ is $C_3$–$C_5$alk-2-en-1-yl, $C_3$–$C_5$alk-2-yn-1-yl or 2-halo-$C_3$–$C_5$alkyl, $R_2$ is hydrogen and $R_3$ is di-$C_1$–$C_4$alkylaminomethyl, or $R_2$ and $R_3$ together are methylene, $R_4$ is hydrogen and $R_5$ is $C_1$–$C_4$alkyl, or a pharmaceutically acceptable salt thereof.

9. A method of treatment according to claim 1, wherein there is selected a compound of formula I wherein $R_1$ is $C_3$–$C_7$alk-2-en-1-yl or 2-halo-$C_3$–$C_7$alkyl, $R_2$ is hydrogen and $R_3$ is di-$C_1$–$C_4$alkylaminomethyl, or $R_2$ and $R_3$ together are methylene, $R_4$ is hydrogen and $R_5$ is $C_1$–$C_4$alkyl, or a pharmaceutically acceptable salt thereof.

10. A method of treatment according to claim 1, wherein the compound of formula I is selected from the group consisting of 3-methallyl-2-(3-methyl-4-oxo-thiazolidin-2-ylidenehydrazono)-5-methylene-thiazolidin-4-one, 3-allyl-2-(3-methyl-4-oxo-thiazolidin-2-ylidenehydrazono)-thiazolidin-4-one, 3-allyl-2-(3-methyl-4-oxo-thiazolidin-2-ylidenehydrazono)-5-methylene-thiazolidin-4-one, 3-methallyl-2-(3-methyl-4-oxo-thiazolidin-2-ylidenehydrazono)-5-dimethylaminomethyl-thiazolidin-4-one, 3-methallyl-2-(3-methyl-5-hydroxy-4-oxo-thiazolidin-2-ylidenehydrazono)-5-methyl-thiazolidin-4-one, 2-(5-acetoxy-3-methyl-4-oxo-thiazolidin-2-ylidenehydrazono)-3-methallyl-5-methyl-thiazolidin-4-one, 3-methallyl-2-(3-methyl-5-pivaloyloxy-4-oxo-thiazolidin-2-ylidenehydrazono)-5-methyl-thiazolidin-4-one, 3-methallyl-2-(3-methyl-5-sulfoxy-4-oxo-thiazolidin-2-ylidenehydrazono)-5-methyl-thiazolidin-4-one, 3-methallyl-2-(3-methyl-5-trimethylsilyloxy-4-oxo-thiazolidin-2-ylidenehydrazono)-5,5-dimethyl-thiazolidin-4-one, 3-methallyl-2-(3-methyl-5-tributylsilyloxy-4-oxo-thiazolidin-2-ylidenehydrazono)-5-methyl-thiazolidin-4-one, methyl[3-methyl-2-(3-allyl-4-oxo-thiazolidin-2-ylidenehydrazono)-4-oxo-thiazolidin-5-yl]phosphate, methyl[3-methyl-2-(3-allyl-5-methyl-4-oxo-thiazolidin-2-ylidenehydrazono)-4-oxo-thiazolidin-5-yl]phosphate, 3-methallyl-2-{3-methyl-5-[tertiary butyl(dimethyl)silyloxy]-4-oxo-thiazolidin-2-ylidenehydrazono}-5-methyl-thiazolidin-4-one, methyl[3-methyl-2-(3-allyl-5,5-dimethyl-4-oxo-thiazolidin-2-ylidenehydrazono)-4-oxo-thiazolidin-5-yl]phosphate, 3-methallyl-2-{3-methyl-5-[tertiary butyl(dimethyl)silyloxy]-4-oxo-thiazolidin-2-ylidenehydrazono}-5,5-dimethyl-thiazolidin-4-one, 3-methallyl-2-(3-methyl-5-triisopropylsilyloxy-4-oxo-thiazolidin-2-ylidenehydrazono)-5-methyl-thiazolidin-4-one, 3-methallyl-2-{3-methyl-5-[(2,3-dimethylbut-2-yl)(dimethyl)silyloxy]-4-oxo-thiazolidin-2-ylidenehydrazono}-5-methyl-thiazolidin-4-one, methyl[3-methyl-2-(3-methallyl-5(R*)-methyl-4-oxo-thiazolidin-2-ylidenehydrazono)-4-oxo-thiazolidin-5(R*)-yl]phosphate, 5-hydroxymethyl-3-methallyl-2-(3-methyl-4-oxo-thiazolidin-2-ylidenehydrazono)-thiazolidin-4-one, phosphoric acid diemthylamide-[3-methyl-2-(3-methallyl-5-methyl-4-oxo-thiazolidin-2-ylidenehydrazono)-4-oxo-thiazolidin-5-yl]ester,

[3-methyl-2-(3-methallyl-5-methyl-4-oxo-thiazolidin-2-ylidenehydrazono)-5-thiazolidin-5-yloxy]-2-oxo-1,3,2-oxazaphospholidine, 3-methallyl-2-(4-oxo-thiazolidin-2-ylidenehydrazono)-thiazolidin-4-one, 3-allyl-2-(3-methyl-5-hydroxy-4-oxo-thiazolidin-2-ylidenehydrazono)-thiazolidin-4-one, 3-methallyl-2-(3-allyl-5-hydroxy-4-oxo-thiazolidin-2-ylidenehydrazono)-5,5-dimethyl-thiazolidin-4-one, 3-(but-3-en-2-yl)-2-(4-oxo-thiazolidin-2-ylidenehydrazono)-thiazolidin-4-one, 3-methallyl-2-(3-methyl-4-oxo-thiazolidin-2-ylidenehydrazono)-5-methyl-thiazolidin-4-one, 3-(but-3-en-2-yl)-2-(3-methyl-4-oxo-thiazolidin-2-ylidenehydrazono)-thiazolidin-4-one, 3-methallyl-2-(3-methyl-4-oxo-thiazolidin-2-ylidenehydrazono)-thiazolidin-4-one, 3-methallyl-2-(4-oxo-thiazolidin-2-ylidenehydrazono)-thiazolidin-4-one, 3-methallyl-2-(3-allyl-4-oxo-thiazolidin-2-ylidenehydrazono)-5,5-dimethyl-1-oxo-thiazolidin-4-one, 3-allyl-2-(3-methyl-4-oxo-thiazolidin-2-ylidenehydrazono)-1-oxo-thiazolidin-4-one, 3-methallyl-2-(3-allyl-1,4-dioxo-thiazolidin-2-ylidenehydrazono)-5,5-dimethyl-1-oxo-thiazolidin-4-one, 3-allyl-2-(3-methyl-1,4-dioxo-thiazolidin-2-ylidenehydrazono)-thiazolidin-4-one, dimethyl[3-methyl-2-(3-methallyl-5-methyl-4-oxo-thiazolidin-2-ylidenehydrazono)-4-oxo-thiazolidin-5-yl]phosphate, 3-(prop-2-ynyl-2-(3-methyl-4-oxo-thiazolidin-2-ylidenehydrazono)-thiazolidin-4-one, and methyl[3-methyl-2-(3-methallyl-5-methyl-4-oxo-thiazolidin-2-ylidenehydrazono)-4-oxo-thiazolidin-5-yl]phosphate, or a pharmaceutically acceptable salt thereof.

* * * * *

UNITED STATES PATENT AND TRADEMARK OFFICE
CERTIFICATE OF CORRECTION

PATENT NO.  : 5,177,091
DATED       : January 5, 1993
INVENTOR(S) : FEIGE ET AL

It is certified that error appears in the above-identified patent and that said Letters Patent is hereby corrected as shown below:

Claim 1, Column 16, line 10 delete structural formula 1 and insert in lieu thereof

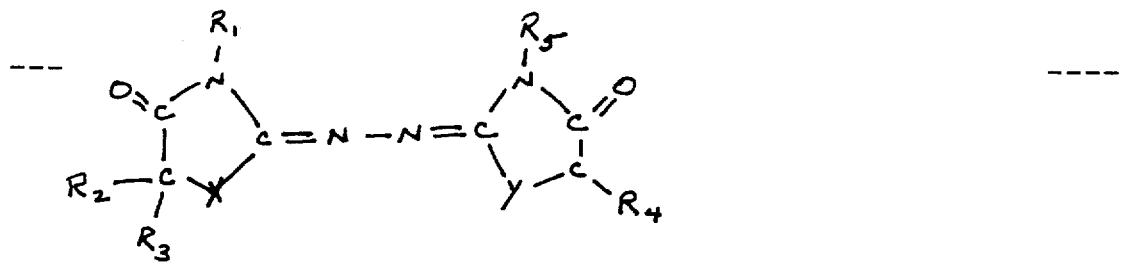

Claim 6, column 17, line 56 change "alkylsilyoxy" to --alkylsilyloxy--

Claim 10, column 19, line 1 change "diemthylamide" to --dimethylamide--

Signed and Sealed this

Second Day of November, 1993

Attest:

BRUCE LEHMAN

Attesting Officer

Commissioner of Patents and Trademarks